US00PP15561P2

(12) United States Plant Patent
Hoogendoorn

(10) Patent No.: US PP15,561 P2
(45) Date of Patent: Feb. 15, 2005

(54) ***DIASCIA* PLANT NAMED 'KIEDITWO'**

(50) Latin Name: *Diascia×hybrida*
Varietal Denomination: Kieditwo

(75) Inventor: Leo Hoogendoorn, Ambacht (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 10/820,505

(22) Filed: Apr. 7, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Diascia* plant named 'Kieditwo', characterized by its compact and outwardly spreading to trailing plant habit; freely branching habit; freely flowering habit; bright pink-colored flowers with darker pink-colored centers; and long flowering period.

1 Drawing Sheet

Botanical classification/cultivar designation: *Diascia×hybrida* cultivar Kieditwo.

BACKGROUND OF THE INVENTION

The present Invention relates to a new and distinct cultivar of *Diascia* plant, botanically known as *Diascia×hybrida,* and hereinafter referred to by the cultivar name Kieditwo.

The new *Diascia* is a product of a planned breeding program conducted by the Inventor in Ambacht, The Netherlands. The objective of the breeding program is to create new compact *Diascias* with numerous flowers and attractive flower coloration.

The new *Diascia* originated from a cross-pollination made by the Inventor in 2000 of two unnamed proprietary *Diascia×hybrida* seedling selections, not patented. The new *Diascia* was selected as a single plant from the resulting progeny of the cross-pollination by the Inventor in 2000 in an controlled environment in Ambacht, The Netherlands.

Asexual reproduction of the new cultivar by terminal cuttings in a controlled environment in Ambacht, The Netherlands since 2001 has shown that the unique features of this new *Diascia* are stable and reproduced true to type in successive generations.

SUMMARY OF THE INVENTION

Plants of the cultivar Kieditwo have not been observed under all possible environmental conditions. The phenotype may vary somewhat with variations in environment such as temperature and light intensity without, however, any variance in genotype.

The following traits have been repeatedly observed and are determined to be the unique characteristics of 'Kieditwo'. These characteristics in combination distinguish 'Kieditwo' as a new and distinct cultivar of *Diascia:*

1. Compact and outwardly spreading to trailing plant habit.
2. Freely branching habit.
3. Freely flowering habit.
4. Bright pink-colored flowers with darker pink-colored centers.
5. Long flowering season.

Plants of the new *Diascia* are more freely flowering than plants of the parent selections. In addition, plants of the new *Diascia* and the parent selections differ in flower color as plants of the parent selections have red purple-colored flowers.

Plants of the new *Diascia* can be compared to plants of the cultivar Pink Queen, not patented. In side-by-side comparisons conducted in Ambacht, The Netherlands, plants of the new *Diascia* differed from plants of the cultivar Pink Queen in the following characteristics:

1. Plants of the new *Diascia* were more freely flowering than plants of the cultivar Pink Queen.
2. Plants of the new *Diascia* had larger flowers than plants of the cultivar Pink Queen.
3. Flower color of plants of the new *Diascia* was brighter pink than flower color of plants of the cultivar Pink Queen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Diascia.*

The photograph at the bottom of the sheet comprises a side perspective view of a typical flowering plant of 'Kideitwo' grown in a container.

The photograph at the top of the sheet comprises a close-up view of a typical inflorescence of 'Kieditwo'.

DETAILED BOTANICAL DESCRIPTION

The aforementioned photographs and following observations and measurements describe plants grown in Lompoc, Calif., in a polycarbonate-covered greenhouse during the winter with day temperatures ranging from 21 to 24° C., night temperatures ranging from 15 to 18° C., and light levels ranging from 4,000 to 8,000 foot candles. Plants were grown for about seven weeks with one plant per 12.5-cm container.

Color references are made to The Royal Horticultural Society Colour Chart, 1995 Edition, except where general terms of ordinary dictionary significance are used.

Botanical classification: *Diascia×hybrida* cultivar Kieditwo.

Parentage:

*Female parent.*—Unnamed proprietary *Diascia×hybrida* seedling selection, not patented.

*Male parent.*—Unnamed proprietary *Diascia×hybrida* seedling selection, not patented.

Propagation:

*Type cutting.*—Terminal vegetative cuttings.

*Time to initiate roots, summer and winter.*—About one week at 21° C.

*Time to produce a rooted young plant, summer and winter.*—About two weeks at 21° C.

*Root description.*—Fine, fibrous; white in color.

*Rooting habit.*—Freely branching.

Plant description:

*Form.*—Compact and outwardly spreading to trailing plant habit. Freely branching with lateral branches potentially forming at every node. Moderately vigorous growth habit.

*Plant height.*—About 20 cm.

*Plant diameter.*—About 39 cm.

*Lateral branches.*—Appearance: Thin, wiry. Length: About 28 cm. Diameter: About 2 mm. Internode length: About 2.75 cm. Texture: Smooth, glabrous. Color: 144A.

*Foliage description.*—Arrangement: Opposite; simple. Length: About 3 cm. Width: About 2.5 cm. Shape: Deltoid. Apex: Broadly acute. Base: Cordate. Margin: Broadly serrate. Texture, upper and lower surfaces: Smooth, glabrous. Venation pattern: Pinnate; arcuate. Color: Developing foliage, upper surface: 144A. Developing foliage, lower surface: 147B. Fully expanded foliage, upper surface: 146A. Fully expanded foliage, lower surface: 147B. Venation, upper and lower surfaces: 146B. Petiole length: About 7 mm. Petiole diameter: About 1 mm. Petiole color: 146A.

Flower description:

*Flower type and habit.*—Solitary zygomorphic flowers arranged on terminal racemes. Five modified petals fused at base: two upper (banner) petals, two lateral petals, and one larger lower lip petal. Flowers not persistent. Flowers face mostly outwardly.

*Quantity.*—Freely flowering; typically about 18 buds and flowers per lateral branch.

*Natural flowering season.*—Long flowering period; plants typically flower during the spring and early summer in the Northern Hemisphere; flowering continuous during this period.

*Flower longevity on the plant.*—About four to five days.

*Fragrance.*—Not detected.

*Inflorescence size.*—Length: About 17 cm. Width: About 5.5 cm.

*Flower size.*—Length: About 2 cm. Width: About 1.7 cm. Depth: About 1.1 cm.

*Flower buds (showing color).*—Length: About 5 mm. Diameter: About 6 mm. Shape: Roughly spherical. Color: 51C.

*Petals.*—Quantity/arrangement: Five modified petals fused at base: two upper (banner) petals, two lateral petals, and one larger lower lip petal. Base of banner petals with concave yellow eyespots; lower surfaces of lateral petals modified into nectar spurs; and lower lip petal convex forming a roughly horizontal insect landing platform. Length: Banner petals: About 7 mm. Lateral petals: About 7 mm. Lower lip petal: About 1.2 cm. Width: Banner petals: About 5 mm. Lateral petals: About 6 mm. Lower lip petal: About 1.3 cm. Lateral petal spur: Length: About 6 mm. Diameter, at petal attachment: About 2 mm. Shape, all petals: Roughly spatulate. Apex, all petals: Rounded. Margin, all petals: Entire. Texture, all petals, upper and lower surfaces: Smooth, satiny. Color, all petals: When opening, upper surface: 51B. When opening, lower surface: 54C. Fully opened, upper surface: 55B; towards base, 54A. Fully opened, lower surface: 55B to 55C. Nectar spurs: 54C. Eyespot on banner petals: 14A.

*Sepals.*—Arrangement/appearance: Single whorl of five sepals fused at base; star-shaped. Length: About 5 mm. Width: About 1 mm. Shape: Elliptic. Apex: Acute. Margin: Entire. Texture, upper and lower surfaces: Smooth, glabrous. Color, upper and lower surfaces: 146A.

*Peduncles.*—Length: About 6 cm. Width: About 1.5 mm. Angle: Upright to about 45° from vertical. Strength: Moderately strong. Texture: Smooth, glabrous. Color: 144A.

*Pedicels.*—Length: About 2.5 cm. Width: Less than 1 mm. Angle: About 45° from the peduncle. Strength: Moderately strong; slender. Texture: Smooth, glabrous. Color: 144B.

*Reproductive organs.*—Stamens: Quantity per flower: Four. Anther shape: Ovoid. Anther length: Less than 1 mm. Anther color: 12A. Pollen amount: Scarce. Pollen color: 12A. Pistils: Quantity per flower: One. Pistil length: About 4 mm. Style length: About 2 mm. Style color: 144D. Stigma shape: Rounded. Stigma color: 144B. Ovary color: 145A.

*Fruit/seed.*—Fruit and seed production has not been observed.

Disease/pest resistance: Plants of the new *Diascia* have not been noted to be resistant to pathogens or pests common to *Diascia*.

Temperature tolerance: Plants of the new *Diascia* have been observed to tolerate temperatures from 0 to 38° C.

It is claimed:

1. A new and distinct cultivar of *Diascia* plant named 'Kieditwo', as illustrated and described.

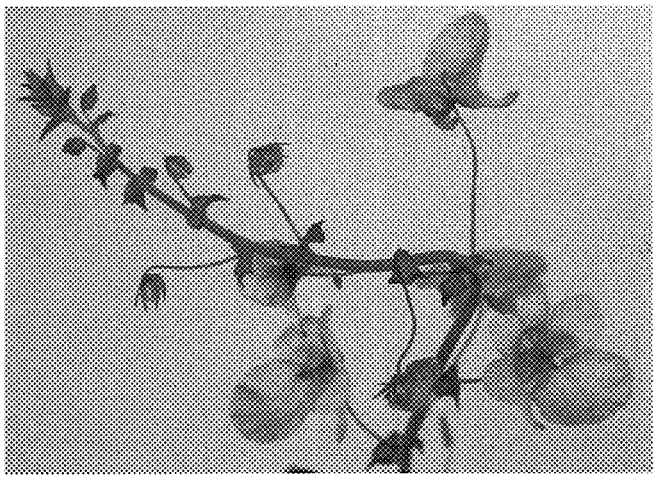
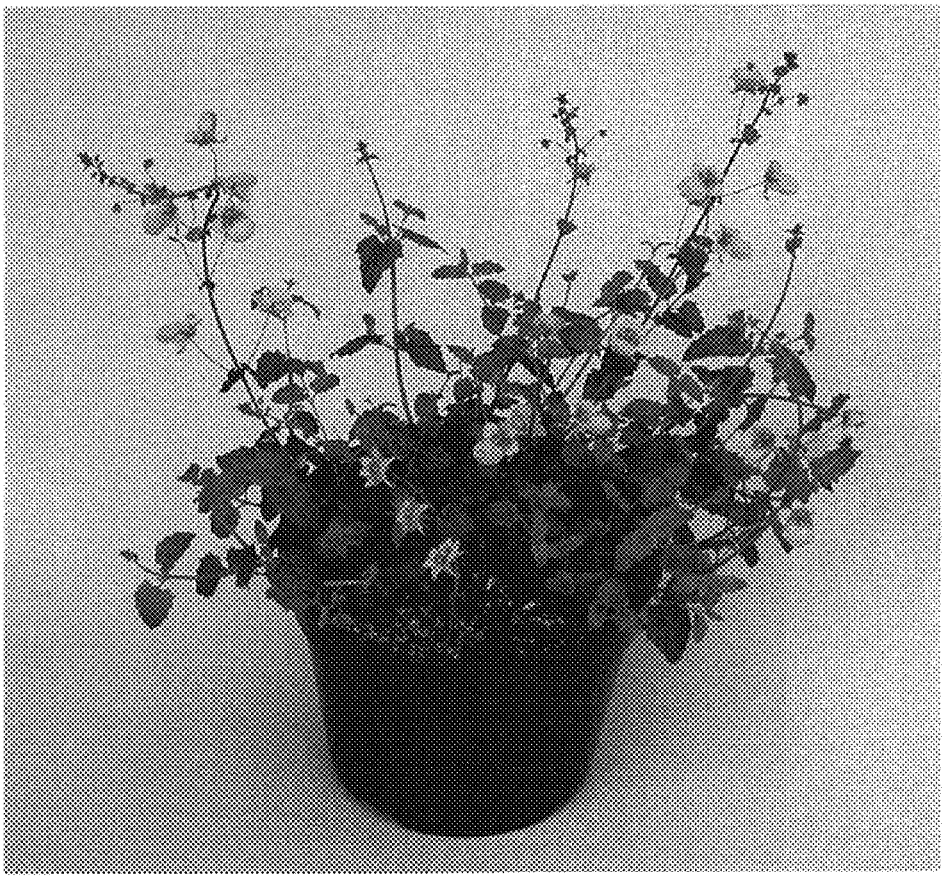

* * * * *